United States Patent [19]

Condo et al.

[11] Patent Number: 5,059,261

[45] Date of Patent: Oct. 22, 1991

[54] PROCESSING OF MATERIALS USING RUPTURABLE MICROCAPSULATES CONTAINING DETECTION MATERIALS

[75] Inventors: Albert C. Condo, Newtown Square; Bernard M. Kosowski, King of Prussia, both of Pa.

[73] Assignee: Mach I Inc., King of Prussia, Pa.

[21] Appl. No.: 526,832

[22] Filed: May 22, 1990

[51] Int. Cl.[5] ...................... C06B 21/00; G01N 33/22

[52] U.S. Cl. ................................ 149/19.92; 149/123; 149/109.6; 264/3.1; 436/56

[58] Field of Search .......................... 264/3.1, 3.2, 3.3; 149/109.6, 123; 436/56

[56] References Cited

U.S. PATENT DOCUMENTS

| | | | |
|---|---|---|---|
| H761 | 4/1990 | Quinlan | 264/3.1 |
| 3,469,439 | 8/1969 | Roberts et al. | 73/88 |
| 4,101,501 | 7/1978 | Hinterwaldner | 260/40 |
| 4,528,354 | 7/1985 | McDougal | 528/3.3 |
| 4,844,845 | 7/1989 | Clarke et al. | 264/3.1 |

*Primary Examiner*—Brooks H. Hunt
*Assistant Examiner*—Daniel J. Jenkins
*Attorney, Agent, or Firm*—William C. Long

[57] ABSTRACT

The present invention relates to the improved processing of materials wherein microcapsules containing a microencapsulated detection agent are combined with the components to be mixed; the microcapsules are designed to rupture at predetermined conditions, and the mixtures are monitored for the presence of the detection agent which indicates that the predetermined conditions were achieved.

3 Claims, 4 Drawing Sheets

RUPTURE PRESSURE CONTOURS

NOTE: SCHEMATIC DIAGRAM OF MELT INDEX PLASTOMETER.

NOTE: ME/RED DYE RUPTURE POINT VERSUS EXTRUSION TEMPERATURE.

PROCESSING OF MATERIALS USING RUPTURABLE MICROCAPSULATES CONTAINING DETECTION MATERIALS

BACKGROUND OF THE INVENTION

1. Field of the Invention

The present invention relates to the processing of materials wherein calibrated sensors comprising microcapsules which contain detection materials ar incorporated with the materials to be processed, the microcapsules being adapted to rupture at predetermined processing conditions with release of detectable amounts of the detection material, this providing an indication that the predetermined conditions had been equaled or exceeded.

Although the invention has wide application in the mixing of materials, for example in the food industry, in extrusion, in extruder design and calibration, and the like, the invention is especially useful in the continuous mix processing of solid rocket fuel and plastic bonded explosives. In this preferred practice of the invention, a microencapsulated, readily detectable material such as a dye is incorporated with the conventional solid fuel components during mixing of the components in, for example, a twin screw extruder. The microcapsules are formulated to rupture when shear rates exerted on the fuel components exceed predetermined levels with the release of the detectable material. Through the use of appropriate monitoring, appearance of the detectable material can be determined evidencing the fact of the microcapsules rupture, and the mixing process can be slowed or halted before shear rates become so high as to be hazardous. Similarly, in other mixing and/or extrusion applications, the calibrated sensors are formulated to rupture at certain conditions, thus enabling materials processing to be controlled.

2. Description of the Prior Art

The use of large solid fuel rocket motors is essential to space and military programs of the United States and other countries. These rocket motors may contain tens of thousands of pounds of fuel, the components of which must be carefully and accurately mixed and loaded into the motor.

Generally speaking, laborious and expensive batch techniques have in the past been employed. Solid fuel components have been batch mixed in vats in quantities of up to 27,000 pounds and the resulting mixtures loaded into rocket motors. Such procedures have been hazardous, and, where uniformity or quality was not satisfactory, entire batches were wasted.

Continuous mixing techniques, for example employing extruders, have inherent advantages over batch techniques. Much smaller quantities are present at any one time in the mixer, thus reducing hazards. Monitoring and sampling are facilitated, and in this way quality control can be greatly improved.

There are, however, problems with the continuous mixing of solid rocket fuel components since the fuels are combustible and potentially explosive. In extruder-type continuous mixers, there always is the danger that the fuel components will be subjected to excessive shear rates causing localized overheating and potential safety problems.

The present invention addresses these problems and provides a method for determining shear rate during the continuous mixing of the solid rocket fuel components whereby operation can be controlled to achieve high throughput and to avoid unsafe conditions.

In the food industry, for example, excessive shear rates during mixing can impart unacceptable taste to the mixed product resulting in substantial amounts of product being unsuitable for sale.

In polymer extrusion processes, it is frequently important to avoid excessive shear rates in order to prevent overheating and/or discoloration of extruded material.

The concept of microencapsulating detectable materials is not novel. For example, U.S. Pat. Nos. 3,016,308 and 3,179,600 describe the use of such materials in "carbonless paper". U.S. Pat. No. 3,469,439 describes the use of microencapsulated color components to measure and record forces over a surface. The microcapsules size and wall characteristics are controlled to provide groups of microcapsules which break at different pressures. Explosives have been tagged by means of vapor fumeable microcapsules containing volatile fluorinated materials; see U.S. Pat. No. 4,399,226. Explosives have also been tagged by addition of luminescent material according to U.S. Pat. No. 3,835,782, by addition of magnetic material according to U.S. Pat. Nos. 4,363,678, 4,198,307, and 4,152,271. Other patents having to do with tagging explosives include U.S. Pat. Nos. 4,018,635, 4,131,064 and 3,772,200. However, this prior art does not relate to the use of microencapsulated sensors in detecting changes in shear conditions and pressures involved with mixing or extruding various materials.

SUMMARY OF THE INVENTION

In accordance with the invention, microcapsules are prepared by known procedures, the capsules having encapsulated therein a material which is detectable upon release from the microcapsules after rupture of the capsule walls. These are the calibrated sensors employed in the present invention. The microcapsules are formulated such that the wall will rupture upon being subjected to predetermined conditions which in turn depend upon the particular application. For rocket fuels, for example, the microcapsules employed rupture upon being subjected to a predetermined shear rate which is above normal but below the rate at which hazards are encountered in the fuel components mixing. During continuous mixing, the rocket fuel is monitored for the detectable material, the detection of which indicates that the predetermined shear rate has been reached at which rupture of the microcapsules occurs. The mixing rate can then be adjusted or mixing can be stopped and the equipment cleaned without overheating and the resulting hazards which were encountered in prior operations. Similarly, in other applications such as extrusion, capsules are used which are adapted to rupture upon being subjected to certain predetermined conditions.

DETAILED DESCRIPTION OF THE INVENTION

Figure 1:
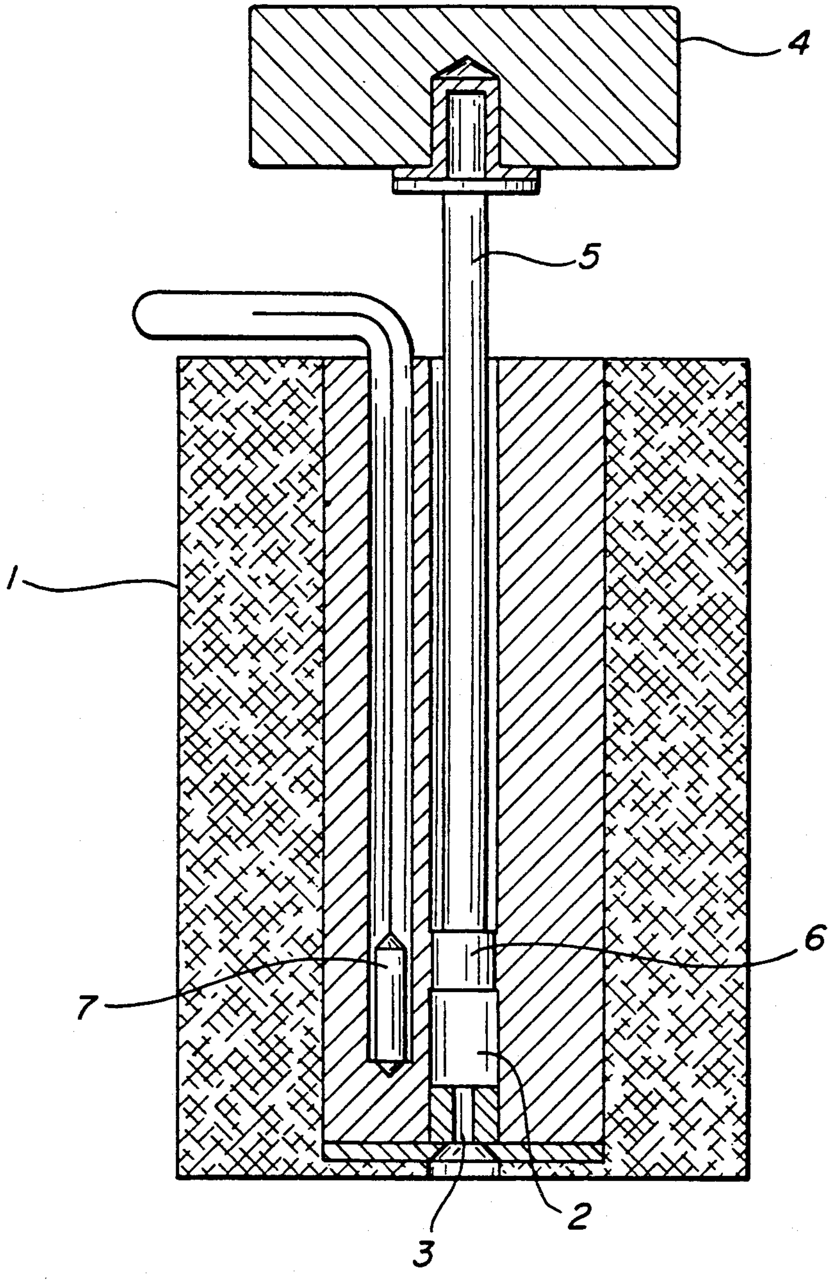
FIG. 1 is a schematic description of a melt index plastometer used in experiments in accordance with the invention.

The detectable component contained in the microcapsule calibrated sensors which are employed in the invention is one which can be detected by conventional means. Color indicating materials such as dyes can suitably be used. Upon rupture of microcapsules containing a dye, the dye is released and imparts a characteristic color to the material being mixed, e.g. rocket fuel components, which can be detected, for example, by visual monitoring. Materials detectable by other than color change can also be used. Photoluminescent materials, laser dyes, leuco dyes, materials which provide a characteristic odor, and the like, are examples of appropriate agents which can be microencapsulated and used according to the invention. Several different detection agents ca be used together to provide redundancy in detection and thus improved reliability. In addition to monitoring by human observation of color and/or odor, instrument monitoring for detection of the release of the detectable material from the microcapsules can be employed.

The microcapsules employed in the invention are prepared in accordance with conventional preparation procedures such as are described in U.S. Pat Nos. 3,016,308, 3,179,600 and 3,469,439.

The invention is advantageously practiced in connection with mixing of components of rocket fuels and plastic bonded explosives (PBX). Such fuels are, by now, well known and generally involve a binder component, an oxidizer and a solid fuel component. Illustrative binders include polysulfides, polyurethanes, polyethers, polyesters, polybutadienes, copolymers of butadiene and acrylic acid, terpolymers of butadiene, acrylic acid and acrylonitrile, carboxy-terminated polybutadiene, hydroxy-terminated polybutadiene, and the like. Ammonium perchlorate is the most commonly used oxidizer; ammonium nitrate is also used. Aluminum is the most common solid fuel; metal hydrides are sometimes used. High energy explosives such as RDX-HMX can be used. Other components can include ballistic modifiers such as iron oxide or ferrocene derivatives and physical characteristic modifiers such as plasticizers and bonding agents.

Illustrative compositions and properties of typical polymer-based cast composite propellants are shown, for example, in Table 12 of Kirk-Othmer, "Encyclopedia of Chemical Technology", 3rd Edition, Volume 9, pages 658–9 (1980). The present invention is practiced with special advantage in the continuous formulation of such composite propellants as well as in various other applications.

While solid rocket fuels are formulated and used as propellents, plastic bonded explosives (PBX) are formulated and used as munitions. PBX's are traditionally manufactured in batch mixers, which is labor intensive and often results in accumulation of large quantities of sensitive materials in the mixer and at other process locations. PBX's consist of various compositions depending on the type and purpose of the munition. Formulations include energetic materials such as explosives, energetic plasticizers and binder ingredients.

As example, PBXH106 consists of the following:

| INGREDIENT | FUNCTION | WEIGHT % |
|---|---|---|
| Sym-Cyclotrimethylene-trinitramine (RDX) | | |
| Type B, Class I | Energetic Solid | 60.00 |
| Type B, Class II | Energetic Solid | 15.00 |
| Ferric Acetylacetonate | Cure Agent | 0.02 |
| Phenyl-B-Naphthylamine | Antioxidant | 0.25 |
| Bis(2,2-dinitropropyl)-acetal | Plasticizer | 18.39 |
| 1,1,1-Tris(hydroxymethyl)-propane | Binder Ingredient | 0.48 |
| Polyoxyethylene glycol | Binder Ingredient | 4.46 |
| Tolyene-2,4-diisocyanate | Cure Agent | 1.40 |

Another example of a munitions composition is that of PBXN109.

| INGREDIENT | FUNCTION | WEIGHT % |
|---|---|---|
| Sym-Cyclotrimethylene-trinitramine (RDX) Type B, Class I | Energetic Solid | 64.00 |
| Aluminum Powder | Metal Powder | 20.00 |
| Hydroxy-terminated poly-butadiene | Binder Ingredient | 7.35 |
| Di(2-hydroxyethyl)dimethyl-hydantoin | Bonding Agent | 0.26 |
| 2,2'-Methylenebis(4-methyl-6-tertiary-butyl-phenol) | Antioxidant | 0.10 |
| Di(2-ethylhexyl)adipate | Plasticizer | 7.35 |
| Dibutyltin dilaurate | Cure Agent | 0.01 |
| Isophorone diisocyanate | Cure Agent | 0.95 |

For further information on PBX formulations and problems related to mixing of formula ingredients can be found in *Status of Twin Screw Processing of Plastic Bonded Explosives* by O. H. Dengel and F. M. Gallantl, Naval Surface Warfare Center, Silver Spring, Md., Contract N60921-86-C-0015, 1986.

The amount of the microencapsulated detection agent is sufficiently small so as not to have a significant deleterious effect on the properties of the materials being processed, e.g. rocket fuel or PBX characteristics. Generally, it is preferred to use amounts of microencapsulated detection agent of less than 2% by weight of the material being processed, preferably less than 1%. Amounts as low as 0.1% can be used depending upon the sophistication of the detection system.

The detection agents are microencapsulated by conventional procedures which involve oil in water or water in oil emulsification techniques. Generally speaking, organic solvent solutions of the detection material ar the preferred microencapsulated agent since upon microcapsule wall rupture these solutions readily permeate the fuel binder or polymer extrudate, or the like, and can be readily detected, e.g., by measurable change in color. In these cases, oil in water microencapsulation procedures are employed to encapsulate the detection agent.

The microcapsules are produced in accordance with known procedures by first forming a stable emulsion of droplets of the detection agent solution in an aqueous continuous phase of the film-forming material which will comprise the microcapsule wall. Such procedures are well known. The microcapsule size can be regulated quite closely by adjustment of the time and speed of mixing during emulsification. In accordance with the invention, it is preferred that the microcapsules be less than about 1,000 microns in diameter, preferably 10 to 500 microns. In order to obtain a narrowly defined detection point, it is preferred to use microcapsules having a narrow particle size distribution, e.g. 20 to 30 microns, and uniform wall thickness.

The core detection agent containing material preferably comprises 50 to 98% by weight of the microcapsules, most preferably 75 to 95%. The following table provides calculated wall thicknesses for microcapsules of different diameters over a broad range of core material weight percentage.

TABLE 1

| Capsule Diameter, Microns | 95% Core | 90% Core | 85% Core | 80% Core | 75% Core |
|---|---|---|---|---|---|
| | Wall Thickness, Microns | | | | |
| 1.0 | 0.01 | 0.02 | 0.03 | 0.04 | 0.05 |
| 2.0 | 0.02 | 0.039 | 0.45 | 0.07 | 0.09 |
| 5.0 | 0.04 | 0.09 | 0.13 | 0.13 | 0.23 |
| 10.0 | 0.08 | 0.17 | 0.26 | 0.36 | 0.46 |
| 20.0 | 0.17 | 0.35 | 0.53 | 0.72 | 0.91 |
| 50.0 | 0.42 | 0.86 | 1.32 | 1.79 | 2.29 |
| 100.0 | 0.85 | 1.73 | 2.64 | 3.58 | 4.57 |
| 200.0 | 1.70 | 3.45 | 5.27 | 7.17 | 9.14 |
| 300.0 | 2.54 | 5.18 | 7.91 | 10.75 | 13.72 |
| 400.0 | 3.39 | 6.90 | 10.55 | 14.34 | 18.29 |
| 500.0 | 4.24 | 8.63 | 13.18 | 17.92 | 22.86 |
| 600.0 | 5.09 | 10.35 | 15.82 | 21.50 | 27.43 |
| 700.0 | 5.93 | 12.08 | 18.46 | 25.09 | 32.00 |
| 800.0 | 6.78 | 13.80 | 21.09 | 28.67 | 36.58 |
| 900.0 | 7.63 | 15.53 | 23.73 | 32.26 | 41.15 |
| 1000.0 | 8.48 | 17.26 | 26.37 | 35.84 | 45.72 |

Conventional wall-forming materials are employed. An essential feature of the materials is that walls which are formed around the detection agent are impermeable to the detection agent and/or solvent carrier. A partial listing of suitable wall materials includes cellulose derivatives, acrylic resins, ethylene copolymers and terpolymers, polysulfones, polycarbonates, polyphenylene oxide, polyamide, polyesters, urea-melamine formaldehyde, urea-resorcinol formaldehyde, polyureas, polyurethanes, polyvinyl alcohol, polyacrylamide, gelatin and the like. Wall thickness of the microcapsules is very important as is composition of the wall-forming material in formulating microcapsules which will rupture at the appropriate conditions. Wall thickness is a function of microcapsule diameter and the volume ratio of core material to wall material. Reducing microcapsule diameter and/or increasing the ratio of core material to wall material results in microcapsules of reduced wall thickness, while increasing microcapsule diameter and/or reducing the ratio of core material to wall material increases wall thickness. The relationship of these parameters is shown by the following expression:

$$\text{Wall Thickness} = d/2[1-(\text{wall vol./core vol.}+1)^{-\frac{1}{3}}]$$

where d=microcapsule diameter.

As above described, the wall-forming material must satisfy certain criteria. The material must provide a wall which is impermeable with regard to the encapsulated dye solution. In addition, the wall must have characteristics such that it will rupture at the predetermined conditions. Wall-forming materials which are used are of a known type, as above described. In general, for a particular system, the appropriate ratio of detection material to wall-forming material and the appropriate curing conditions can readily be determined by empirical means. For example, by a few simple tests, conditions for the formation of suitable calibrated sensor microencapsulated detection agent for use in a particular application and which rupture at proper conditions can readily be determined.

The conditions at which the microcapsules are designed to rupture will depend on a number of factors including the nature and relative amounts of the materials which are mixed and the type of mixing means which are employed. For fuel formulations, twin screw extruders are the preferred mixing means, and the components other than the microcapsules are conventional in type and proportions. It is preferred to employ detection agent containing microcapsules which rupture at about 500 psi or lower, preferably 100 to 300 psi.

In preparation of the microcapsules, the detection agent, preferably together with solvent carrier, is emulsified in a continuous phase containing the wall-forming material. Relative amounts of core detection agent and solvent and wall-forming material are selected in order to provide microcapsules of the desired final composition. The emulsion is agitated to provide droplets of the appropriate size and uniformity. Temperature and pH can be adjusted and additives employed according to known technology.

If desired, additional wall-forming material or cross-binding agents can be added to the emulsion to insure the appropriate final properties. The droplets can be cured and are then dried, preferably by spray drying, to produce the final free-flowing powder.

The following illustrate the invention:

Microcapsules of a xylene solution of an Automate Red B dye (Morton Thiokol) were synthesized and were tested in accordance with the present invention. The dye solution was based on 10 grams of dye per 100 ml. xylene; Automate Red B was selected based on its ability to permeate a selected PBX simulant mix which was used in these tests. The capsule wall material was a melamine-urea-phenolic polymer. Characteristics of the microcapsules were as follows:

TABLE 2

| Sample Number | Core (Weight Percent) | Wall Diameter (Microns) | Wall Thickness (Microns) |
|---|---|---|---|
| 9-87 | 85.3 | 20-60 | 0.71 |
| 91-B | 85.7 | 50-110 | 1.37 |
| 11-17 | 89 | 20-50 | 0.45 |
| 11-18 | 85.8 | 5-25 | 0.26 |
| 11-19 | 80.1 | 20-50 | 0.87 |
| 11-20 | 89.3 | 50-110 | 1.01 |
| 11-22 | 85.6 | 20-50 | 0.61 |
| 11-39A | 81.1 | 20-53 | 0.71 |
| 11-39B | 88.7 | 53-75 | 0.71 |
| 11-39C | 91.9 | 75-106 | 0.71 |
| 11-39D | 93.6 | 106-125 | 0.71 |
| 11-39E | 94.6 | 125-150 | 0.71 |

A PBX simulant mix was selected comprised of alpha-alumina together with hydroxy terminated polybutadiene binder (HTBP) or a mixture of HTBP and dioctyl sebacate (DOS) or dioctyl adipate (DOA) in accordance with procedures adopted by earlier workers. See Wang, F. *Fluorescence of Polymer Flows,* DTIC Report No. SBU 675, DTIC Format SB05A, Accession No. DNO 56686, 2 Sept. 1987, National Bureau of Standards, Polymer Division, Gaithersburg, Md. and Bur, A., Wang, F. W. and Dehl, R. E., *In Situ Florescence Monitoring of the Viscosities of Particle Filled Polymers in Flow,* Annual Report, Contract No. N00014-86-F-0115, Jan. 1988, National Bureau of Standards, Gaithersburg, Md.

Mixtures of PBX simulant and calibrated sensor, microencapsulated Red Dye, were extruded in a Melt Index Plastometer which is a standard instrument for measuring the melt flow of polyethylene at standard conditions of temperature, pressure or shear. FIG. 1 is a schematic drawing of the apparatus. The instrument consists of an insulated thermostatically controlled steel cylinder with a 2.0-inch (5.08 cm) OD reservoir 2 and a 90-degree exit angle to a 0.0825-inch (2.1 mm) orifice 3. Adding weight 4 to an external rod 5 drives the piston 6 inside the cylinder and forces PBX simulant mix through the orifice at rates of about 0.15 to 900 g/10 minutes, depending on melt viscosity and drive pressure. A 10 g/minute flow rate would be equivalent to 60 lb/hr throughput in a twin screw extruder with a 30 mm (1.18 inch) diameter bore. Temperature measuring means 7 is provided.

Typically, the weight of resin sample (such as polyethylene) extruded through the orifice in a 10-minute period at 190 degrees C. (374 degrees F.) is called the "melt index." The test is usually run on polyethylene in accordance with ASTM test method D-1238-57T. The "melt index" value for polyethylene is related to its molecular weight. For varying molecular weights, different weights must be placed on the piston to drive sufficient resin through the orifice to get a valid extrudate weight measure. In this case, a typical extrusion environment is present.

The melt index plastometer is similar in principle to the capillary flow apparatus described by Bur, et al., above cited. The pressure is measured by dividing the weight of the flow drive plunger plus added weights to induce flow by the area of the plunger face or cross sectional area of the barrel. The shear rate experienced by the PBX simulant flowing through the capillary is varied by changing pressure. The classical capillary flow equation applies:

$$\nu = \frac{\pi R^4}{8Q} \cdot \frac{\Delta P}{L} \quad (1)$$

$\nu$=viscosity of the simulant
R=radius of the Capillary
$\Delta$P=applied pressure—atmospheric pressure or the pressure drop across the capillary
L=length of the capillary
Q=flow rate $$\gamma = \frac{4Q}{\pi R^3} \quad (2)$$

$\gamma$=shear rate ($sec^{-1}$)
From Equation (1) is derived:

$$\nu = \left(\frac{\pi R^3}{4Q}\right)\left(\frac{R}{2}\right)\frac{\Delta P}{L} \quad (3)$$

and, applying Equation (2), $$\nu = \frac{R\Delta P}{\gamma 2L} \quad (4)$$

$$\Delta P = \frac{\nu\gamma 2L}{R} \quad (5)$$

From Equation (4), it can be seen that the shear rate ($sec^{-1}$) is directly related to the P (psi) for a given melt or PBX simulant viscosity and capillary radius. As the capillary radius, R, is decreased, P must be increased for a given flow rate at constant viscosity.

Alpha-alumina (4–18 micron particle size range) was mixed with HTPB at the weight ratio of aluminia/binder of 85/15. The mix was loaded with ½ weight percent calibrated sensor microencapsulated Red Dye (ME/Red Dye) and the opaque grey pasty mix (containing dispersed unruptured ME/Red Dye particles) was inserted into the melt index apparatus. The mix was pressured by weight to force it through the 2.1 mm wide orifice at room temperature of 78 degrees F.

The following Table 3 shows the results obtained:

TABLE 3

| psi | Appearance of Extrudate |
|---|---|
| 43 | opaque (with unruptured Red ME/dye particles present) |
| 200 | opaque (with unruptured Red ME/Dye particles present) |
| 300 | pink coloration |
| 374 | definitive discoloration |

From this data it can be seen that when the PBX simulant containing the microencapsulated Red Dye Lot Number 9-87 was subjected to applied pressure of 300–374 at room temperature, microcapsule rupture occurred which imparted detectable color to the simulant mixture.

It should be noted that the percentage of calibrated sensors rupturing can be conveniently calibrated by admixing unencapsulated Red Dye with the PBX simulant mix in amounts corresponding to that in various percentages of the calibrated sensor microcapsules to provide standard coloration representing release of predetermined portions of the encapsulated Red Dye.

Process test data were obtained by extrusion of the 85/15 alpha-alumina/HTPB PBX simulant mix, with 0.5 weight percent ME/Red Dye added, in the previously described melt index plastometer at 78 degrees F. and 58 degrees F. The addition of 0.5 weight percent ME/Red Dye reduced the alumina/binder weight ratio from 85/15 to 84.75/14.75.

The PBX simulant mix formulation had the consistency of "putty" with 14.75 weight percent HTPB binder. At less than 14.75 percent, the mixture viscosity was too low to run in the melt index plastometer. Table 4 provides data that shows the effect of extrusion pressure on coloration of extrudate due to rupture of ME/Red Dye capsules.

It is seen from the data that significant microcapsule rupture became evident between 374 and 473 psi. Actual visual inspection by the technician at the time of the run placed the "break" point at 432 psi. This is indicated in Table 4 as moderate color change "mod.(L)" for extrudate at 58 degrees F.

When comparing the two lot 9-91B runs at 78 degrees F. and 58 degrees F., in Table 4, the effect of lowering the process temperature is to decrease the required pressure for capsule rupture from about 532 psi at 78 degrees F. to about 432 psi at 58 degrees F. It is believed that this is due to a viscosity difference.

TABLE 4

RUPTURE OF ME/RED DYE MICROCAPSULES DUE TO EXTRUSION PRESSURE EFFECT OF TEMPERATURE AND PARTICLE SIZE

Color Development

TABLE 4-continued

| RUPTURE OF ME/RED DYE MICROCAPSULES DUE TO EXTRUSION PRESSURE EFFECT OF TEMPERATURE AND PARTICLE SIZE | in Extrudate | |
|---|---|---|
| ME/Dye Lot Number | 9-91B | 9-91B |
| Particle Diameter | 50–110 | 50–110 |
| Wall Thickness | 1.37 | 1.37 |
| Temperature (degrees F.) | 78 | 58 |
| Pressure (psi) | | |
| 122 | none | none |
| 182 | none | none |
| 243 | none | v.v.sl. |
| 300 | none | v.sl. |
| 374 | none | sl. |
| 432 | v.v.sl. | mod.(L) |
| 473 | — | mod. |
| 495 | v.sl. | mod. |
| 532 | v.sl. | mod. |
| 576 | v.sl. | mod. |
| 617 | v.sl. | mod. |
| 700 | est mod.(L) | — |

| Ingredient | Weight Percent |
|---|---|
| Alpha Alumina | 84.75 |
| HTPB | 14.75 |
| ME/Red Dye | 0.50 |

Tests of ME/Red Dye lots 9–91B and 11–17 in PBX simulant were run in duplicate. Both show a good reproducibility of observed ME/Dye rupture pressures.

Comparison of runs 11–17, 11–19 and 11–22 show a definitive relationship of increased ME/Dye rupture pressure as capsule wall thickness is increased for a given particle diameter. A similar trend is shown in runs 9–91B and 11–20.

Comparison of runs 11–19 and 11–20 indicates that variance in particle size at relatively similar wall thicknesses shows a substantially lower rupture pressure for the larger particle size.

TABLE 5

RUPTURE OF ME/RED DYE MICROCAPSULES DUE TO EXTRUSION PRESSURE EFFECT OF MICROCAPSULE WALL THICKNESS AND DIAMETER (WIDE RANGE)

| ME/Dye Lot | 9-87 | 9-91B | 9-91B | 11-17 | 11-17 | 11-18 | 11-19 | 11-20 | 11-22 |
|---|---|---|---|---|---|---|---|---|---|
| Particle Dia., Microns | 20–60 | 50–110 | 50–110 | 20–50 | 20–50 | 5–25 | 20–50 | 50–110 | 20–50 |
| Wall Thickness, Microns | 0.71 | 1.37 | 1.37 | 0.45 | 0.45 | 0.26 | 0.87 | 1.01 | 0.61 |
| Temperature, Degrees (F.) | 57 | 57 | 58 | 57 | 58 | 57 | 58 | 58 | 57 |
| Pressure (psi) | | | | | | | | | |
| 43 | — | — | — | — | — | — | — | none | — |
| 76 | — | — | — | v.v.sl. | v.v.sl. | — | — | v.sl. | — |
| 100 | none | none | none | v.v.sl. | v.v.sl. | — | — | — | — |
| 122 | none | none | none | v.sl. | v.sl. | — | — | none | — |
| 156 | none | none | none | sl. | sl. | v.v.sl. | none | — | — |
| 182 | none | none | v.v.sl. | mod(L) | sl. | v.sl. | none | mod.(L) | none |
| 243 | v.v.sl. | v.v.sl. | v.sl. | mod. | mod(L) | mod(L) | — | — | v.v.sl. |
| 300 | v.v.sl. | v.sl. | sl. | — | — | mod. | sl. | — | — |
| 374 | v.sl. | sl. | mod.(L) | mod.+ | — | mod.+ | mod. | — | v.sl. |
| 473 | mod.(L) | mod.(L) | mod.+ | — | mod.+ | — | mod.(L) | — | sl. |
| 576 | mod. | — | dark | — | — | — | — | — | est. mod.(L) |
| 617 | dark | — | — | — | — | — | — | — | — |

| Ingredient | Weight Percent |
|---|---|
| Alpha-Alumina | 87.75 |
| HTPB | 5.875 |
| DOS | 5.875 |
| ME/Red Dye | 0.50 |

For subsequent experiments, a 50/50 weight ratio mix of HTPB/DOS was used as the binder material. This is consistent with typical binder usage in PBX formulations and imparts a polarity to the binder for improved dye permeation from ruptured capsules.

To obtain a viscosity having the consistency of putty, as was the case for the 85/15 alpha-alumina/HTPB mix of Table 5, the alpha-alumina content in the HTPB/DOS binder was increased to 88 weight percent.

Table 4 provides data showing the effect of extrusion pressure on color change of extrudate due to rupture of the ME/Red Dye microcapsules. The ME/Red Dye rupture pressure is indicated as the "mod,(L)" designation, which suggests a light moderate color change.

Generally, the data suggest that ME/Red Dyes with rupture pressures in the 40–100 psi range would require large particle diameter with relatively thin capsule walls. This is believed to be typical of PBX extrusion pressure at the die for a typical PBX mix in the NSWC Werner and Pfleiderer millimeter twin screw extruder. Other energetic material mixing such 35 millimeter as LOVA and propellants are believed to experience higher pressures at the respective die orifices.

ME/Red Dye rupture data in Tables 4 and 5 are based on qualitative inspection of extrudate as it emerged from the melt index plastometer 2.1 mm diameter die orifice.

The ME/Red Dye rupture levels were estimated by comparing color levels to neat mixtures of the PBX simulant and dye. Table 6 shows the relationship between percent capsule rupture and the visual inspection rating.

TABLE 6

CORRELATION OF PERCENT ME/RED DYE RUPTURE COLORIMETRIC STANDARDS TO QUALITATIVE INSPECTION RATING OF EXTRUDATES

| Percent Rupture | Applied Visual Rating |
|---|---|
| 0 | none |
| 8.5 | v.v.sl. |
| 17.6 | v.sl. |
| 18.4 | slight |
| 34.1 | mod.(L) |
| 53.9 | dark |

TABLE 6-continued

CORRELATION OF PERCENT ME/RED DYE RUPTURE COLORIMETRIC STANDARDS TO QUALITATIVE INSPECTION RATING OF EXTRUDATES

| Percent Rupture | Applied Visual Rating |
|---|---|
| 72.9 | v. dark |
| 88.0 | v.v. dark |

It was concluded from this correlation regarding the extrudates shown in Tables 4 and 5 that significant ME/Red Dye capsule rupture occurred at a rating designated as "mod.(L)"-meaning just past the empirically accepted failure point or at a point where ME/-Dye rupture is believed to be about 40 percent.

Figure 2:
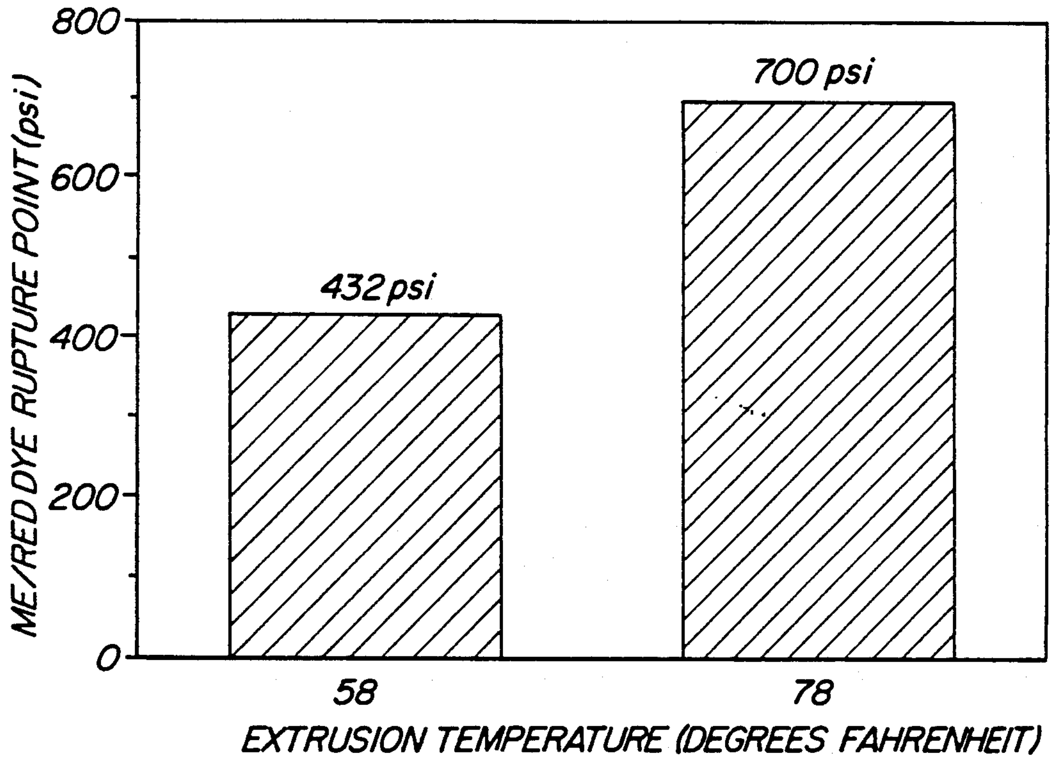
FIG. 2 is a plot of microcapsule rupture point vs. extrusion temperature in accordance with the invention.
Figure 3:
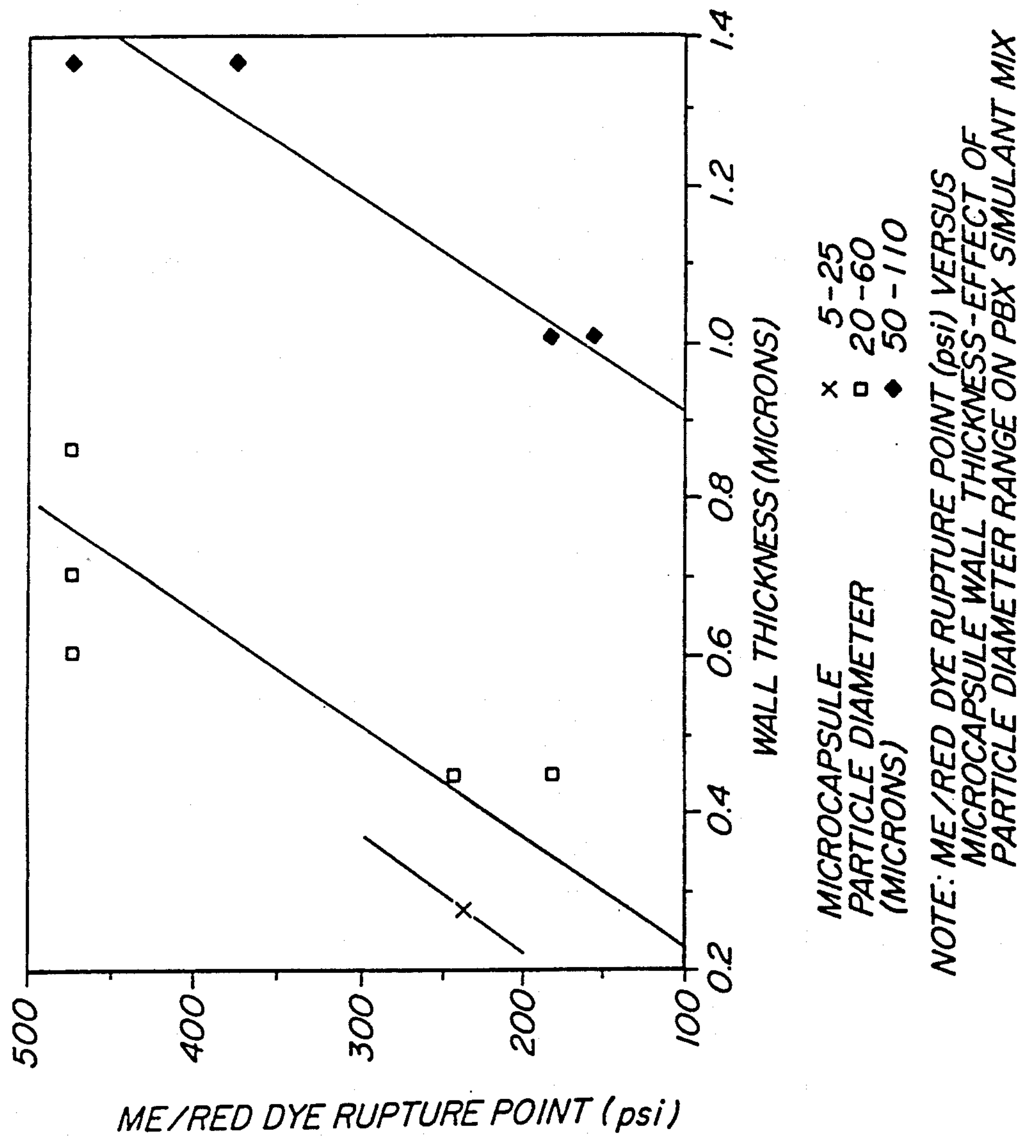
FIG. 3 is a plot of microcapsule rupture point vs. wall thickness showing the effect of particle diameter range in accordance with the invention.

FIGS. 2 and 3 are plots of pressure versus the proposed 40 percent ME/Red Dye rupture point indicated as "mod (L)" in Tables 4 and 5. Inspections of the FIGS. 2 and 3 graphically illustrate the conclusions drawn from Tables 4 and 5.

All ME/Red Dye lots previously discussed had a relatively wide particle diameter range of between 30 to 60 microns, as shown in Table 5.

An attempt was made to fractionate a ME/Red Dye synthesis lot into smaller fractions. This was done with the lot numbers 11-39A through E series. This lot was fractionated to obtain narrow particle size ranges of about 20 to 30 microns. All had calculated wall thickness of about 0.71 microns.

These narrow particle size range ME/Red Dye lots were added to a PBX simulant mix having the same composition as the reported runs in Table 5. Rupture pressures of extrudates are reported in Table 7. Runs using ME/Red Dyes 11-39D and 11-39E were discontinued due to PBX simulant mix viscosity problems. Runs 11-39A to 11-39C reinforce previous findings of the particle size effect at constant wall thickness on microcapsule rupture pressure. Of special interest in the Table 7 data are the observations that the transition from unruptured to ruptured as pressure increases appears to be more sudden or sharp.

TABLE 7

RUPTURE OF ME/RED DYE MICROCAPSULE DUE TO EXTRUSION PRESSURE
EFFECT OF MICROCAPSULE WALL THICKNESS AND DIAMETER
NARROW PARTICLE RANGE CAPSULES

| ME/Dye Lot | 11-39A | 11-39B | 11-39C | 11-39D | 11-39E |
|---|---|---|---|---|---|
| Particle Diameter Microns | 20-53 | 53-75 | 75-106 | 106-125 | 125-150 |
| Wall Thickness Microns | 0.71 | 0.71 | 0.71 | 0.71 | |
| Temperature, degrees F. | 58 | 58 | 58 | 58 | 58 |
| Pressure (psi) | | | | | |
| 43 | none | none | none | none | * |
| 76 | — | v.v.sl. | v.v.sl. | v.v.sl. | |
| 100 | — | — | — | — | |
| 122 | — | v.sl. | v.sl. | v.v.sl. | |
| 156 | none | sl. | v.sl. | sl. | |
| 182 | none | sl. | sl. | sl. | |
| 243 | v.v.sl. | sl. | mod.(L) | mod.(L) | |
| 300 | v.sl. | — | — | — | |
| 374 | sl. | mod.(L) | mod. | mod. | |
| 473 | mod.(L) | — | mod.+ | mod.+ | |
| 576 | — | — | — | — | |
| 617 | | | | | |

| Ingredient | Weight Percent |
|---|---|
| Alpha Alumina | 87.75 |
| HTPB | 5.875 |
| DOS | 5.875 |
| ME/Red Dye | 0.50 |

*Observations were too erratic to make definitive evaluations.

Figure 4:
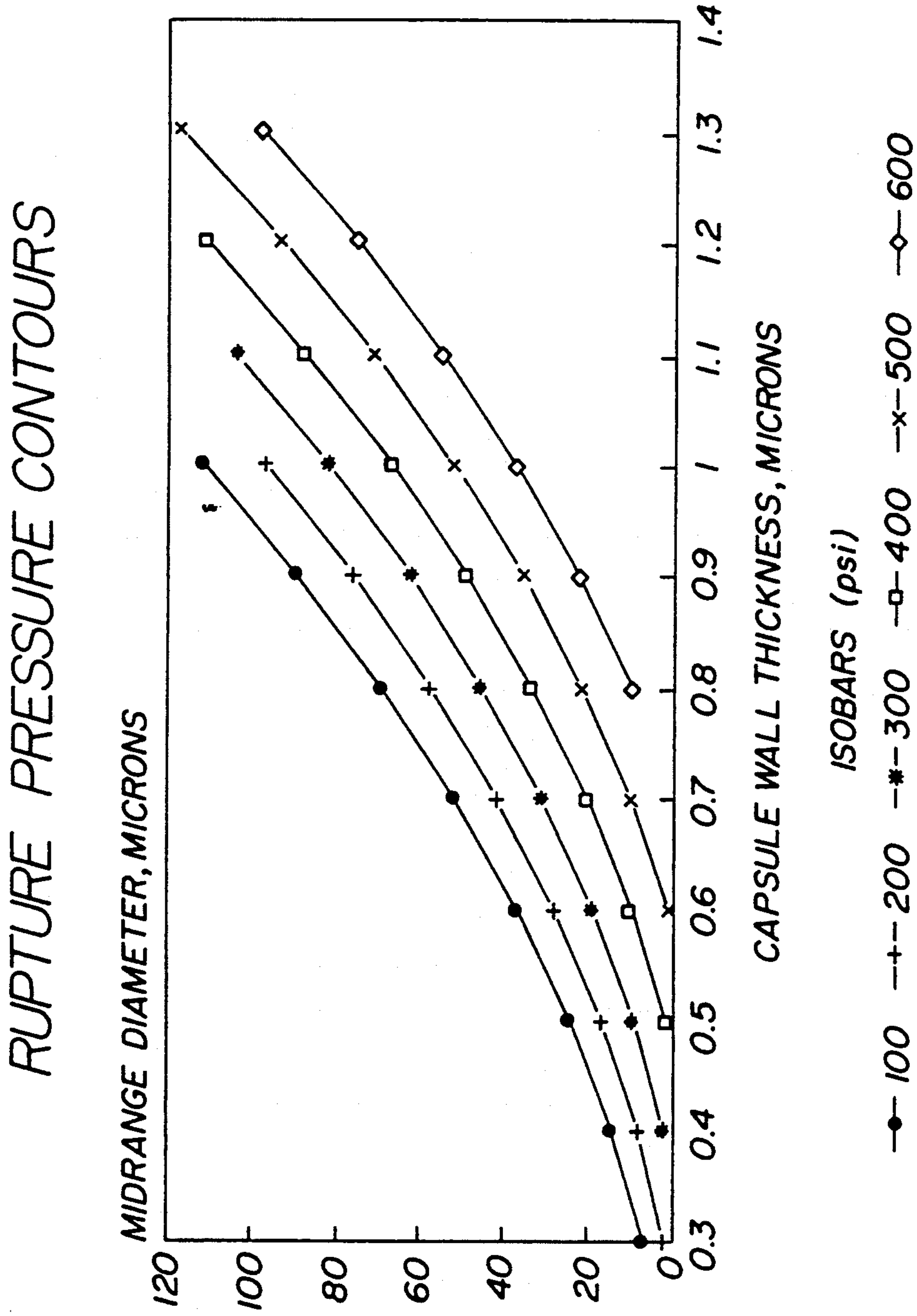
FIG. 4 is a plot showing rupture pressure contours as a function of microcapsule mid-range diameter and wall thickness in accordance with the invention.

FIG. 4 is a plot showing rupture pressure contours as a function of microcapsule mid-range diameter and wall thickness based on a regression analysis of the data in Tables 5 and 6.

What is claimed is:

1. The method of mixing materials which comprises incorporating with the materials being mixed microcapsules containing encapsulated detection agent, the walls of said microcapsules being adapted to rupture at predetermined mixing conditions, and mixing the materials while monitoring the material mixture for the presence of said detection agent.

2. The method of preparing a plastic bonded solid rocket fuel which comprises combining an oxidizer component, a polymeric binder component, a fuel component and microcapsules containing a microencapsulated detection agent, the walls of said microcapsules being adapted to rupture at a predetermined shear rate, mixing said components together with said microcapsules, and monitoring the resulting mixture for the presence of said detection agent.

3. The method of preparing a plastic bonded, solid explosive which comprises an energetic explosive component, an energetic plasticizer component, a polymeric binder component and microcapsules containing a microencapsulated detection agent, the wall of said microcapsules being adapted to rupture at a predetermined shear rate, mixing said components together with said microcapsules, and monitoring the resulting mixture for the presence of said detection agent.

* * * * *

UNITED STATES PATENT AND TRADEMARK OFFICE

CERTIFICATE OF CORRECTION

PATENT NO. : 5,059,261

DATED : October 22, 1991

INVENTOR(S) : Albert C. Condo et al

It is certified that error appears in the above-identified patent and that said Letters Patent is hereby corrected as shown below:

Column 1, line 5, the following should be inserted:

--This invention was made with Government support under support under Contract No. N60921-88-C-0135 awarded by White Oak Laboratory, Naval Surface Warfare Center. The Government has certain rights to this invention.--.

Signed and Sealed this

Twentieth Day of April, 1993

*Attest:*

MICHAEL K. KIRK

*Attesting Officer*

*Acting Commissioner of Patents and Trademarks*